(12) United States Patent
Prim (10) Patent No.: US 7,069,743 B2
(45) Date of Patent: Jul. 4, 2006

(54) SYSTEM AND METHOD FOR RECOVERY OF C2+ HYDROCARBONS CONTAINED IN LIQUEFIED NATURAL GAS

(75) Inventor: Eric Prim, 6310 Deering Dr., Odessa, TX (US) 79762-5160

(73) Assignee: Eric Prim, Odessa, TX (US)

( * ) Notice: Subject to any disclaimer, the term of this patent is extended or adjusted under 35 U.S.C. 154(b) by 681 days.

(21) Appl. No.: 10/079,254

(22) Filed: Feb. 20, 2002

(65) Prior Publication Data

US 2003/0158458 A1    Aug. 21, 2003

(51) Int. Cl.
   *F25J 1/00*    (2006.01)
(52) U.S. Cl. .......................................... 62/620; 62/50.2
(58) Field of Classification Search ................ 62/50.2, 62/618, 620
   See application file for complete search history.

(56) References Cited

U.S. PATENT DOCUMENTS

| | | | | |
|---|---|---|---|---|
| 2,952,984 A * | 9/1960 | Marshall, Jr. | ................ | 62/622 |
| 3,420,068 A * | 1/1969 | Petit | ............................. | 62/623 |
| 3,446,029 A * | 5/1969 | Grgurich et al. | ............. | 62/50.2 |
| 3,837,172 A | 9/1974 | Markbreiter et al. | ........... | 62/24 |
| 3,837,821 A * | 9/1974 | Buffiere et al. | ............ | 48/127.3 |
| 4,274,849 A | 6/1981 | Garier et al. | ..................... | 62/9 |
| 4,445,917 A | 5/1984 | Chiu | ............................. | 62/25 |
| 5,089,034 A | 2/1992 | Markovs et al. | ................ | 55/28 |
| 5,114,451 A * | 5/1992 | Rambo et al. | ................ | 62/623 |
| 5,137,558 A | 8/1992 | Agrawal | ........................ | 62/24 |
| 5,295,350 A | 3/1994 | Child et al. | ................. | 60/39.02 |
| 5,359,856 A * | 11/1994 | Rhoades et al. | .............. | 62/611 |
| 5,363,655 A | 11/1994 | Kikkawa et al. | .................. | 62/9 |
| 5,394,686 A | 3/1995 | Child et al. | ................ | 60/39.02 |
| 5,615,561 A | 4/1997 | Houshmand et al. | ......... | 62/611 |
| 5,685,170 A | 11/1997 | Sorensen | ...................... | 62/625 |
| 6,199,403 B1 | 3/2001 | Cole et al. | .................... | 62/613 |
| 6,510,706 B1 | 1/2003 | Stone et al. | ................... | 62/620 |
| 6,526,777 B1 | 3/2003 | Campbell et al. | ............. | 62/621 |
| 6,564,579 B1 * | 5/2003 | McCartney | ................... | 62/620 |
| 6,564,580 B1 | 5/2003 | Bowen et al. | ................ | 62/623 |

* cited by examiner

*Primary Examiner*—William C. Doerrler
(74) *Attorney, Agent, or Firm*—Conley Rose, P.C.

(57) ABSTRACT

A processing method and system for separating methane-rich and ethane-rich components from an LNG stream. The LNG stream is preheated against a distillation column overhead vapor stream and against an overhead vapor product prior to entering the column. The overhead vapor product is methane-rich. The LNG stream may further be preheated against the column bottoms and another heating medium. The method may also include compressing the methane-rich product, condensing it against the LNG stream, and pumping it. The system may also comprise third and fourth heat exchangers configured to preheat the LNG stream with the bottoms product and the heating medium. Further, the system may provide for compressing the overhead vapor product prior to the its exchanging heat with the LNG stream and a pump for pumping condensed overhead vapor product. Additionally, the system generates all of the required reflux by cross exchanging the column overhead with the incoming LNG stream.

17 Claims, 4 Drawing Sheets

SYSTEM AND METHOD FOR RECOVERY OF C2+ HYDROCARBONS CONTAINED IN LIQUEFIED NATURAL GAS

CROSS-REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The present invention generally relates to systems and methods for processing hydrocarbons. More particularly, the present invention relates to systems and methods for removing a portion of ethane and heavier components from a liquefied natural gas stream.

BACKGROUND OF THE INVENTION

Natural gas is commonly recovered in areas where natural gas production exceeds demand. In these areas, it is economical to convert the vapor natural gas stream into a liquefied natural gas (LNG) stream. LNG can be stored much more efficiently than vapor natural gas, which makes it economical to transport natural gas to areas distant from the mining region. For transportation purposes, LNG is maintained at cryogenic temperatures so as to retain its liquid state. When LNG reaches its final destination, it is typically heated to return the LNG to a vapor state for transmission through natural gas pipelines to consumers.

LNG consists primarily of saturated hydrocarbon components such as methane, ethane, propane, butane, etc. LNG also may contain trace quantities of nitrogen, carbon dioxide, and oxygen. The stream normally contains more than 50 mole % methane. However, the present invention is not limited to a specified composition of LNG.

LNG often has a higher BTU content or a lower dew point than pipeline specifications will allow. Thus, LNG may require processing before it can be introduced into a natural gas pipeline system. Processing generally requires removal of heavier components from the LNG, which consists of predominantly methane with lesser amounts of heavier hydrocarbons, including ethane, propane, butane, pentane, etc. Prior methods of recovery focus on recovery of these heavier components at the final destination of the LNG product, where one aspect of processing is revaporization of the methane stream.

Generally, pipeline specifications for natural gas require a light stream consisting primarily of methane. Similarly, ethane is generally the most volatile component that can be recovered in any substantial quantity for sale as liquefied petroleum gas (LPG). Thus, processing of LNG generally requires splitting LNG into a methane-rich component and an ethane-rich component. Typically, the methane-rich component will be primarily composed of methane, and the ethane-rich component will be primarily composed of ethane and heavier hydrocarbons.

When LNG is processed at its destination point for purposes of shipping, the methane-rich component is typically recovered as a gas for introduction into natural gas pipeline systems, and the ethane-rich component is typically recovered as a liquid for further processing or sale as LPG. This ethane-rich component, or LPG, may also be referred to as natural gas liquid (NGL).

Various methods for recovering LPG from LNG are known. Marshall (U.S. Pat. No. 2,952,984) teaches the use of a distillation column for separating methane from liquefied natural gas. The method produces a vapor methane product. Markbreiter et al. (U.S. Pat. No. 3,837,172) teach a method for processing LNG but without an external energy input for compression. This method also produces a vapor methane stream. Rambo et al. (U.S. Pat. No. 5,114,451) describe a method for processing LNG focused on recovery of ethane and heavier hydrocarbons and on low capital investment. The method also produces a vapor methane stream.

In contrast, the methane-rich component must be recovered as a liquid when LNG is processed at a location prior to reaching its final shipping destination. Recovery as a liquid allows for efficient transportation to the final destination. The prior art techniques do not provide for removal of $C_{2+}$ hydrocarbons from a liquefied gas stream and do not take advantage of significant efficiency improvements that are possible where a liquid methane product stream is desired.

LNG is commonly separated to recover heavier hydrocarbons that may be more valuable as liquid products and to bring the LNG stream into compliance with pipeline specifications for component concentrations, dew point, and/or heating value. Therefore, processing generally involves removal of heavier hydrocarbons to decrease specific gravity and to lower heating value or to recover the heavier hydrocarbons as a liquid product for separate sale.

BRIEF SUMMARY OF THE INVENTION

The present invention overcomes the disadvantages of the prior art where a liquid methane product stream is desired. A preferred embodiment of the present invention compresses the methane product vapor and condenses it against the incoming liquefied natural gas. The compressed methane product liquid can be pressurized with a pump, as opposed to prior art methods of pressurization using compressors, which are energy-intensive. Similarly, by condensing the methane product vapor against the incoming liquefied natural gas, a significant energy savings is realized by avoiding external cooling and by minimizing heat input for distillation column operation.

The present invention differs from previous technologies in that it provides a simple process that produces high ethane recovery at much lower energy consumption and lower capital cost. Energy and capital costs are reduced because the reflux is produced by direct cross exchange with the incoming NGL stream. This configuration eliminates the need for a separate refrigeration compressor for overhead vapor condensation. Furthermore, the more efficient cross exchange provides preheat for the feed stream to the column, thereby reducing the energy requirements needed to accomplish the separation.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

The present invention provides a process that is capable of recovering a methane-rich stream as a liquid from an LNG stream in an efficient and cost-effective manner. While the present invention provides an effective separation, it is not necessary to produce a majority of either component in either stream.

While conventional separations yielding gas-phase methane can be accomplished with a variety of systems for fractionating the LNG into a lighter and a heavier stream, as mentioned above, the present invention comprises a heat transfer arrangement that is very efficient. It provides a system and method for compressing the lighter product that is much more efficient than conventional systems. As a result, a large number of combinations and arrangements are possible to achieve the desired separation, resulting in more or less equipment cost and more or less energy usage. For example, heat may be transferred in a variety of arrangements and in a variety of heat-integration complexities ranging from little or no heat integration to extremely complex and capital cost-intensive heat integration.

Figure 1:
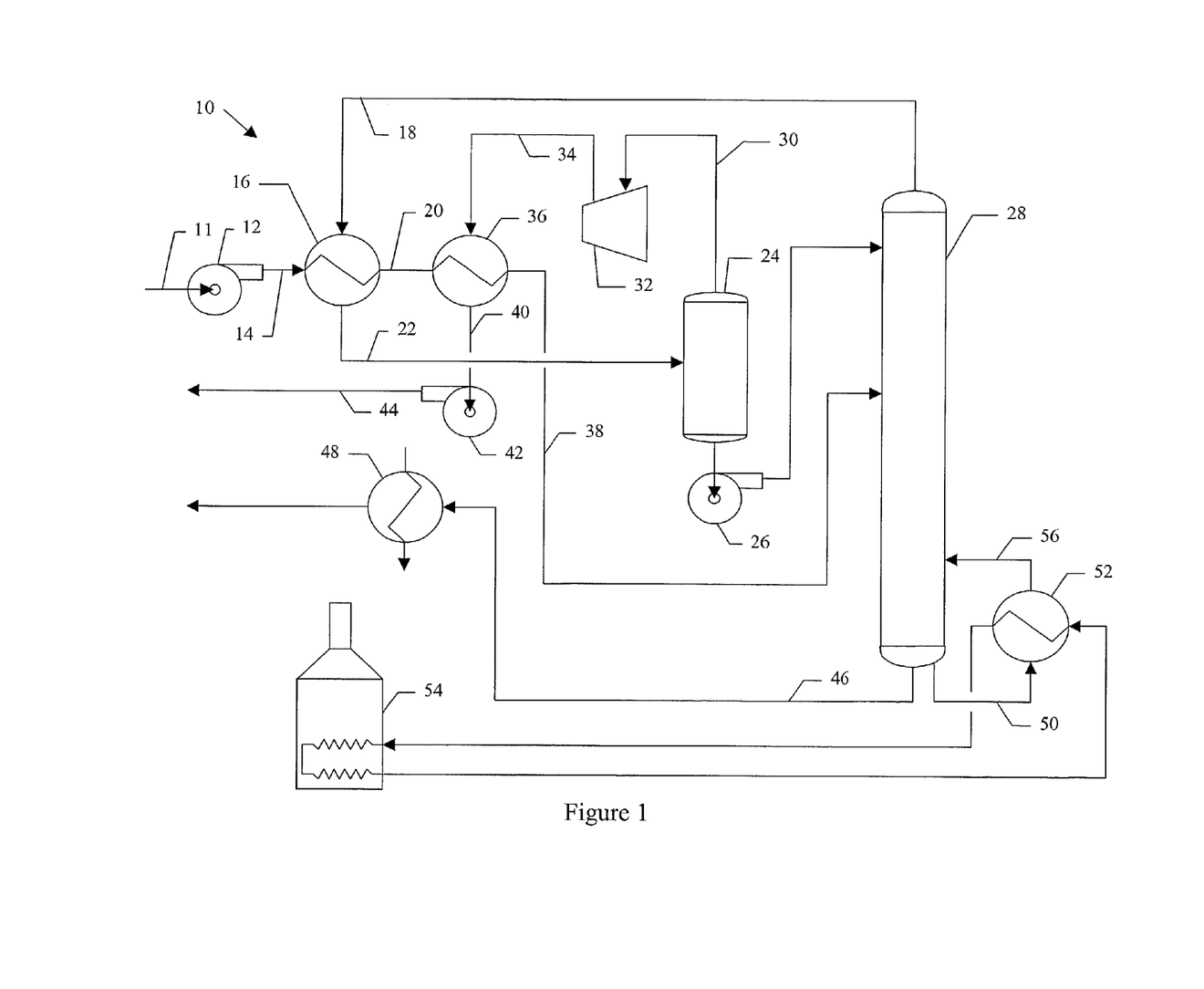
FIG. 1 is a flow diagram showing an LNG processing unit arranged in accordance with a preferred embodiment of the present invention.

Referring now to FIG. 1, an exemplary preferred embodiment of the present invention includes an LNG processing unit 10, a heat exchanger 16, an overhead drum 24, a feed-overhead product heat exchanger 36, and a tower 28. LNG processing unit 10 may be considered to be a distillation system or a fractionation system. Feed stream 11 may be composed of LNG feed to the processing unit. The LNG feed 11 is pressurized by feed pump 12 to feed the unit. LNG may be stored at pressures at or near atmospheric pressure. LNG is typically received at −175° C. to −130° C. (−280° F. to −200° F.) and 300 to 1,700 kPa (50 to 250 psia).

The present process may be accomplished at a broad range of pressures. Preferably, the operating pressure of unit 10 is 2000 to 4000 kPa (200 to 600 psia). This pressure range allows for optimum distillation of the LNG stream and optimum separation with reasonable equipment costs. Thus, the feed pump 12 increases the pressure of feed stream 11 to the operating pressure of the unit, creating pressurized feed stream 14.

Feed pump 12 may comprise one or more pumps of varying types depending upon the specific operating conditions required. For example, feed pump 12 may be a centrifugal, positive displacement, or other conventional pump type. Further, feed pump 12 may be a single stage or multistage centrifugal or other type pump depending upon the pressure differential required. The preferred type of pump for feed pump 12 will depend upon the specific operating conditions of a given application; however, preferably feed pump 12 is a totally enclosed LNG pump. A totally enclosed LNG pump has no external seal, such that if a seal fails the leak is contained, preventing a catastrophic failure. More preferably where pressure differential requires, feed pump 12 is a multistage centrifugal pump totally enclosed LNG pump.

Pressurized feed stream 14 feeds a feed-overhead heat exchanger 16. Pressurized feed stream 14 may be fed to either the shell side or the tube side of feed-overhead heat exchanger 16. Further, heat exchanger 16 can be any type of suitable heat exchanger. Plate-and-frame, shell-and-tube, spiral, hairpin, core, core-and-kettle, double-pipe and other known types of heat exchanger are suitable for use in this application. Either process stream may be used on either process side of any of the exchangers. Preferably, feed-overhead heat exchanger 16 is a core exchanger because a core exchanger can reside in the same cold box unit as other heat exchangers in the unit, which reduces capital cost while increasing energy efficiency.

Feed-overhead heat exchanger 16 preheats pressurized feed stream 14 while condensing overhead vapor stream 18. Latent heat from overhead vapor stream 18 is transferred into pressurized feed stream 14, creating a first heated LNG feed stream 20. Correspondingly, overhead vapor stream 18 is partially condensed in feed-overhead heat exchanger 16, resulting in a condensed overhead vapor stream 22. The amount of overhead vapor stream 18 condensed in feed-overhead heat exchanger 16 may vary with process operating conditions and with the required natural gas specifications. The condensation will preferably be less than 100%, resulting in condensed overhead vapor stream 22 being two-phase (i.e., vapor and liquid).

Condensed overhead vapor stream 22 feeds overhead drum 24. Overhead drum 24 is preferably a horizontal or a vertical cylindrical vessel. Further, overhead drum 24 may be other shapes, but a cylindrical vessel is preferred because cylindrical vessels are the most cost efficient design. Overhead drum 24 is sized to allow separation of the liquid and vapor from the condensed overhead vapor stream 22. The liquid settles into the bottom of overhead drum 24 and is withdrawn from drum 24 by a reflux pump 26. Reflux pump 26 may comprise one or more pumps of various types and in various arrangements. For example, reflux pump 26 may be a centrifugal, positive displacement, or any other type of pump commonly commercially available. Preferably, reflux pump 26 is a centrifugal pump. Reflux pump 26 pumps the liquid portion of condensed overhead vapor stream 22 back to tower 28 for improved separation in tower 28, described in detail below.

The vapor portion of condensed overhead vapor stream 22 is collected in the upper portion of overhead drum 24 and forms an overhead vapor product stream 30. Overhead vapor product stream 30 feeds a compressor 32. Compressor 32 compresses overhead vapor product stream 30 into a compressed overhead vapor product stream 34. Compressor 32 may be of various types, including centrifugal, screw, reciprocating, or any other commonly used industrial compressor type. Preferably, compressor 32 is a centrifugal compressor because of the lubrication problems encountered with other compressors at very low temperatures. Compressor 32 increases the pressure and temperature of overhead vapor product stream 30 for condensation in a feed-overhead product heat exchanger 36. The compressor not only acts to increase the condensing temperature of the overhead stream, it also provides compression heat that is recovered to aid in the separation process. The increase in condensing temperature is necessary to increase the available tempaerture approach in exchanger 36.

Compressed overhead vapor product stream 34 exchanges heat in feed-overhead product heat exchanger 36 with first heated LNG feed stream 20. Thus, feed-overhead product heat exchanger 36 may be considered to be a condenser. Compressed overhead vapor product stream 34 preheats first heated LNG feed stream 20, forming second heated LNG feed stream 38. Compressed overhead vapor product stream 34 gives up latent heat in feed-overhead product heat exchanger 36, resulting in substantial condensation of compressed overhead vapor product stream 34. While substantially all of compressed overhead vapor product stream 34 may be condensed in feed-overhead product heat exchanger 36, it is not necessary to the invention that the entire compressed overhead vapor product stream 34 be condensed. For example, some lighter compounds contained in compressed overhead vapor product stream 34, such as nitrogen, carbon dioxide or oxygen, may not condense and may have to be vented to a flare, to atmosphere, or to further processing equipment. Preferably, however, the entire compressed overhead vapor product stream 34 is condensed in feed-overhead product heat exchanger 36, forming overhead product condensate stream 40.

Feed-overhead product heat exchanger 36 may be a plate-and-frame, shell-and-tube, core, core-and-kettle, double-pipe, spiral, hairpin, or any other type of heat exchanger that is suitable for use in this application. Further, for construction purposes, feed-overhead product heat exchanger 36 may be built in the same cold box as feed-overhead heat exchanger 16. Placing both heat exchangers in a cold box increases energy efficiency with a minimum of capital investment.

Overhead product condensate stream 40 may be fed to overhead product pump 42, which increases the pressure of overhead product condensate stream 40. The pressure is increased sufficiently to allow the discharged overhead product stream 44 to enter a pipeline or other distribution system for further transportation. Overhead product pump 42 may be any of various types of pumps including centrifugal, positive displacement, or other types of industrial pumps. Further, overhead product pump 42 may be single or multistage centrifugal or other pump type depending upon the pressure differential required in the specific service. Preferably, overhead product pump 42 is a totally enclosed LNG pump such that there are no external seals. Enclosing overhead product pump 42 helps prevent a catastrophic failure as with feed pump 12. More preferably where pressure requirements dictate, overhead product pump 42 is a multistage centrifugal totally enclosed LNG pump.

The specific type that is preferred for a given service will depend upon the operating conditions of the specific application. Pipelines typically require between 6,200 kPa and 10,500 kPa (900 PSIA to 1,500 PSIA). Other product destinations may have varying pressure requirements, such as further processing equipment or storage. Pump sizing and selection for this type of operation are well known to those having ordinary skill in the art.

Overhead product pump 42 may or may not be necessary, depending on the processing conditions of tower 28, the operating conditions of compressor 32, and the downstream pressure requirements. A substantial benefit of the present invention, however, is that the pressure of overhead product stream 44 may be increased with pump 42, as opposed to imparting all of the pressure needed for downstream operations with compressor 32. Adding pressure with compressor 32 requires far more energy consumption than adding pressure with overhead product pump 42 because the compression process is inherently less efficient as well as being capital intensive. Also, adding pressure with pump 42 reduces the operating pressure of feed-overhead product heat exchanger 36, allowing a lower design pressure and a less expensive heat exchanger. Therefore, consistent with allowing substantially complete condensation of compressed overhead vapor product stream 34, preferably as much as pressure as possible should be added with overhead product pump 42 as opposed to compressor 32.

Returning to feed-overhead product heat exchanger 36 and continuing with FIG. 1, second heated LNG feed stream 38 leaves feed-overhead product heat exchanger 36 and feeds tower 28. Tower 28 is a distillation column and is preferably a vertical cylindrical vessel containing random or structured packing or trays. Second heated LNG feed stream 38 may enter tower 28 near the center of the trayed or packed section of tower 28. The optimum feed location is determined based upon the composition of second heated LNG feed stream 38 and upon the compositions of the desired overhead and bottoms product streams. This scheme does not rule out the possibility of feeding the column at multiple locations. The calculations are well known to a person having ordinary skill in the art and will not be repeated here.

Tower 28 fractionates second heated LNG feed stream into an overhead vapor stream 18 and a bottoms stream 46. The composition of these streams will depend upon the specifications required of the natural gas product; however, overhead vapor stream 18 preferably consists primarily of methane. More preferably, overhead vapor stream 18 consists of a majority of methane by mole concentration. Ultimately, overhead vapor stream 18 is processed further in the manner described above and as shown in FIG. 1 to form overhead product stream 44. Because overhead product stream 44 is the ultimate overhead product, achieving a correct composition of this stream is a primary goal in the operation of tower 28. Overhead vapor stream 18 undergoes cooling and another flash separation in overhead drum 24 prior to becoming overhead product stream 44. Because of the flash separation, the concentration of methane in overhead product stream 44 will be greater than that in overhead vapor stream 18. Thus, overhead product stream 44 may be referred to as a methane-rich stream. This label is equally applicable to overhead vapor product 30, compressed overhead vapor product stream 34, and overhead product condensate stream 40 because all of these streams have substantially the same composition. It should be remembered, however, that despite the label, it is not necessary for overhead product stream 44 to comprise a majority concentration of methane.

Bottoms stream 46 is the bottoms product of tower 28 and may also comprise a wide range of concentrations but preferably will comprise a majority of ethane and heavier components by mole concentration. Thus, bottoms stream 46 may be referred to as an ethane-rich stream. Bottoms stream 46 will not necessarily comprise a majority concentration of ethane or even of ethane and heavier components, but bottoms stream 46 will preferably comprise a majority of ethane and heavier components by mole concentration. Bottoms stream 46 may be cooled in bottoms cooler 48 prior to going to storage, to further transmission, or to further processing. Cooling may be achieved with refrigeration or with process fluids from neighboring processes. This cooling step will provide Net Positive Suction Head (NPSH) to the bottoms stream which will allow for pumping without the aid of a booster pump. NPSH can be obtained by raising the pressure of an isothermal stream, or by lowering the temperature of an isobaric stream. In this situation lowering the temperature is preferred because it eliminates the use of a booster pump, which lowers maintenance, operation and capital cost. Although this arrangement is preferred, a booster pump can be used in this situation as well.

The compositions of overhead product stream 44 and bottoms stream 46 are controlled by the operation of tower 28. Tower 28 is a distillation column that may be operated in various ways to achieve various separations, depending upon the economics of the operation at a given time and depending upon the product specifications required. To achieve the separation, heat is added at the lower end and heat is removed at the upper end. Heat removal and reflux generation are discussed above with respect to feed-overhead heat exchanger 16, overhead drum 24, and reflux pump 26. Proceeding to heat input, reboiler liquid stream 50 is drawn off of tower 28 at the base of tower 28 for feeding reboiler 52. Reboiler 52 may be any of various types of heat exchangers including kettle, thermosyphon, stab-in tube bundle, or forced circulation furnace.

Reboiler 52 is preferably a thennosyphon or kettle type reboiler as shown in FIG. 1. These types of heat exchangers are driven by gravity flow without the need for additional circulating equipment. Heat from an external source is input into reboiler 52. Preferably, reboiler liquid stream 50 enters the shell side of reboiler 52 to allow for minimum pressure drop on the tower side of reboiler 52. Heat may come from a variety of sources, including a circulating heating system, steam, process streams, hydrocarbons, or other heating mediums such as glycol systems. FIG. 1 indicates the use of a circulating heating system in which a heating fluid is circulated through furnace 54 and through reboiler 52 for heat exchange with reboiler liquid stream 50. Preferably, a circulating glycol heating system is used because glycol will not freeze as quickly as steam condensate in such a service. However, other systems will work as well, such as alcohols, hydrocarbons, or blends such as diesel fuel. Most heating mediums are acceptable, so long as water is avoided because of the likelihood of freezing in the exchanger.

Reboiler liquid stream 50 is at least partially vaporized in reboiler 52 with the vapor and remaining liquid, if any, returning to tower 28 as reboiler return stream 56. The circulation of reboiler liquid stream 50 and reboiler return stream 56 transfers the heat from reboiler 52 into tower 28 creating the driving force for the separation. Separation within tower 28 occurs through intimate contact of vapor and liquid in the tower internals in a manner that is known to one having ordinary skill in the art. Thus, the amount of heat input and heat removal along with the amount of reflux and the diameter of tower 28 for a given feed quantity can are all be determined based upon economics and upon desired product compositions, as is well known in the art.

The result of the apparatus described above is a system and method for transferring heat that was originally input to tower 28 and must be removed from overhead vapor stream 18. The arrangement accomplishes this result with a minimum of equipment cost and a minimum energy usage. LNG processing unit 10 also allows condensation of the methane-rich product against LNG feed without external heat removal, resulting in very high energy efficiency. Further, LNG processing unit 10 allows for highly efficient pressurization of the methane-rich stream. Other arrangements may accomplish similar minimal cost and utility results even more effectively under certain operating conditions.

Figure 2:
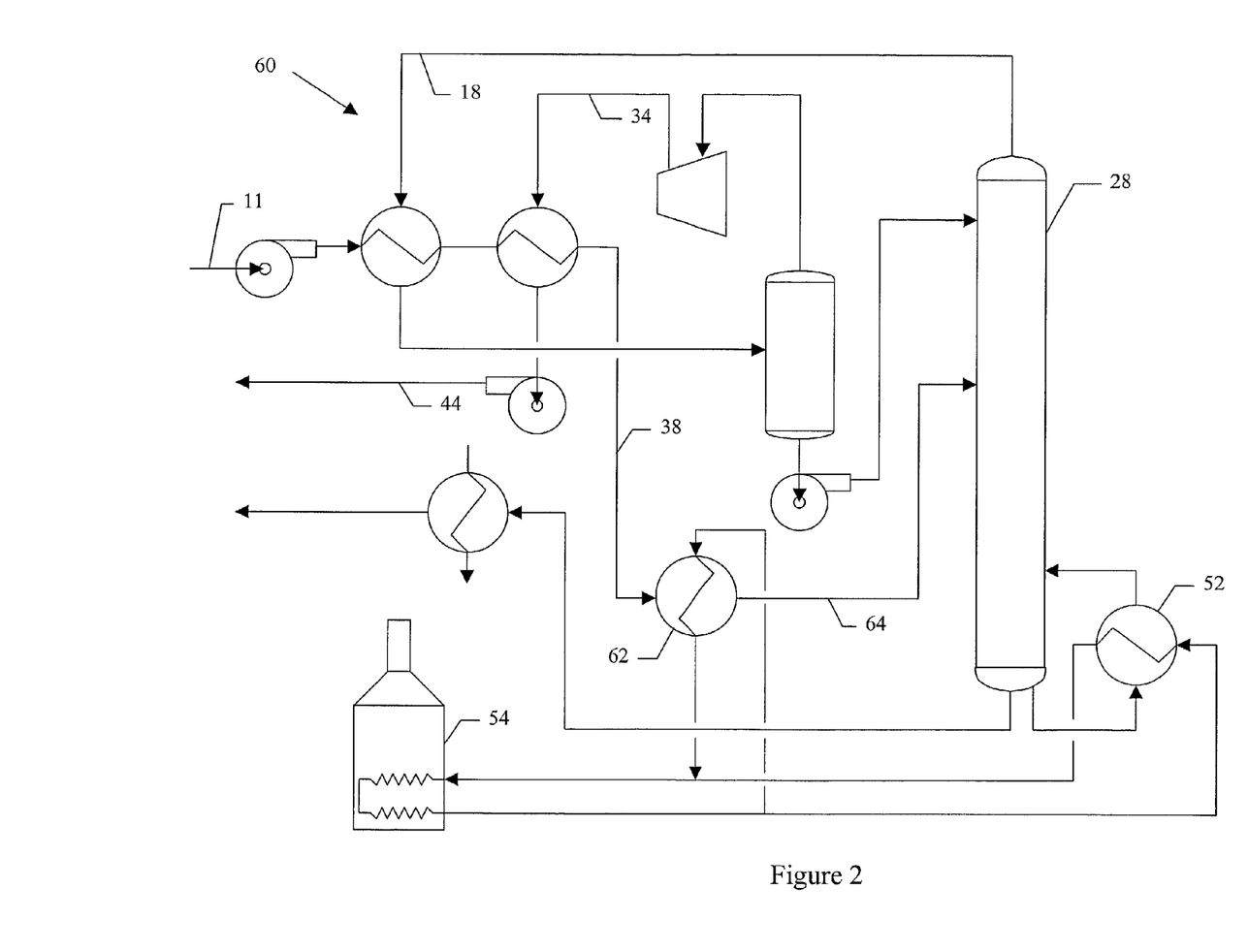
FIG. 2 is a flow diagram of an LNG processing unit arranged in accordance with a preferred embodiment of the present invention and including further feed preheat.

With reference to FIG. 2, one such arrangement is disclosed. The LNG processing unit 60 disclosed in FIG. 2 may be appropriate for different operating conditions or for different product specifications in which overhead vapor stream 18 and compressed overhead vapor product stream 34 are insufficient in quantity or in temperature to heat LNG feed stream 11 to the desired level. Thus, LNG processing unit 60 is distinguished from LNG processing unit 10 in that LNG processing unit 60 contains a feed preheater 62. Feed preheater 62 preheats second heated LNG feed stream 38 further adding more heat for more efficient operation of tower 28.

Feed preheater 62 may be any of various types of heat exchangers. For example, feed preheater 62 may be a plate-and-frame, shell-and-tube, core, core-and-kettle, double-pipe, spiral, hairpin, or any other common industrial type of heat exchanger. Also, the depiction in FIG. 2 is not meant to indicate that any stream is "tube side" or "shell side." Either stream may be on either side of a shell-and-tube exchanger or any side of any other type of exchanger.

Feed preheater 62 may receive heat from any of various sources, including a circulating heating system, steam, process streams, or other heating mediums such as glycol systems. Preferably, as shown in FIG. 2, the system receives heat input from the circulating glycol heating system heated by furnace 54 and used in reboiler 52. However, there is no requirement that the heating system for feed preheater 62 be common with reboiler 52. The two heating services may use a common heat source or different heat sources. Alternatively heat can come from other sources such as turbine exhaust or compression heat.

Heat input from feed preheater 62 produces a tower feed stream 64. Tower feed stream 64 contains more heat than second heated LNG feed stream 38 and under certain operating conditions may allow for tower 28 to be smaller for the same desired separation and feed quantity. Thus, LNG processing unit 60 may require less capital expense than a similar unit without feed preheater 62 under certain operating conditions. Generally, as specifications require overhead product stream 44 to have a higher methane concentration, heat input from compressed overhead vapor product stream 34 and from overhead vapor stream 18 into LNG feed stream 11 will be less, resulting in LNG processing unit 60 being more economical in some instances.

Figure 3:
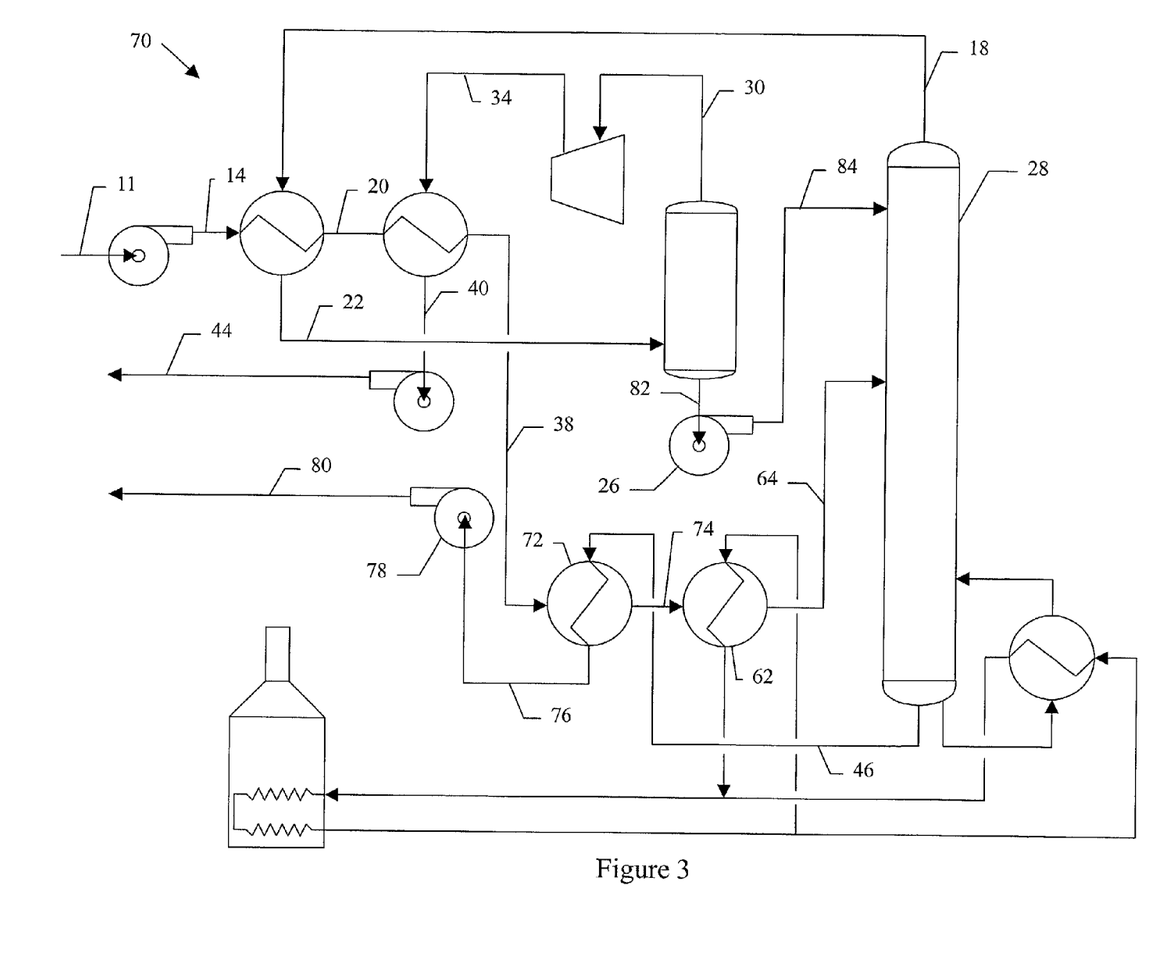
FIG. 3 is a flow diagram of an LNG processing unit arranged in accordance with a preferred embodiment of the present invention and including further heat integration and feed preheat.

With reference to FIG. 3, another embodiment of the present invention comprises an LNG processing unit 70. LNG processing unit 70 addresses the same concern as LNG processing unit 60, in that it provides more heat to LNG feed stream 11 prior to entering tower 28. The goal of LNG processing unit 70 is to put as much heat as possible in the LNG feed stream 11 prior to the LNG feed reaching tower 28. This operation provides for the most efficient design of tower 28 and simultaneously allows for complete condensation of overhead product stream 44 and cooling of bottoms stream 46 without external cooling or refrigeration. In order to accomplish this, LNG processing unit 70 adds feed-bottoms heat exchanger 72. As with the other heat exchangers described above, feed-bottoms heat exchanger 72 may be of any type including plate-and-frame, shell-and-tube, double-pipe, core, core-and-kettle, spiral, hairpin, or any other common industrial type of heat exchanger. Also, as noted above with other heat exchangers, feed-bottoms heat exchanger 72 as shown in FIG. 3 is not limited to any particular arrangement with respect to process streams and sides of the heat exchanger.

Second heated LNG feed stream 38 is further heated in feed-bottoms heat exchanger 72 by bottoms stream 46, which produces third heated LNG feed stream 74. Third heated LNG feed stream 74 is further heated in feed preheater 62 as in LNG processing unit 60. The arrangement of LNG processing unit 70 requires less energy usage in feed preheater 62 to achieve a given feed energy level. Further, by exchanging heat from bottoms stream 46 with second heated LNG feed stream 38, cooled bottoms product stream 76 is produced. Cooled bottoms product stream 76 does not need further cooling; therefore, bottoms cooler 48 of LNG processing units 10 and 60 (see FIGS. 1 and 2) can be eliminated. Elimination of bottoms cooler 48 from alternate embodiments also eliminates the requirement of a cooling utility. Thus, LNG processing unit 70 is a preferred embodiment if economics dictate that feed preheat over that achieved in LNG processing unit 10 is desired.

One further option is shown in LNG processing unit 70. Cooled bottoms product 76 may be sent to storage, to further processing, or to a pipeline for transport to distant locations. If cooled bottoms product 76 needs to be sent to a pipeline, getting cooled bottoms product 76 into the pipeline likely requires a high pressure. Typically, bottoms product flowing out of a distillation column, such as tower 28, will not have sufficient net positive suction head to supply a pump with a large differential pressure. In a service such as this, a pump with a nominal differential pressure is used to create the net positive suction head required to feed a pump with a large differential pressure. Thus, two pumps in series are typically required. One beneficial aspect of the present invention is the elimination of the requirement of dual pumps in series. Because feed-bottoms heat exchanger 72 cools bottoms stream 46, resulting cooled bottoms product stream 76 contains sufficient net positive suction head to feed NGL pump 80. This benefit also extends to LNG processing units 10 and 60 that use cooling other than LNG feed to lower the temperature of bottoms stream 46.

Figure 4:
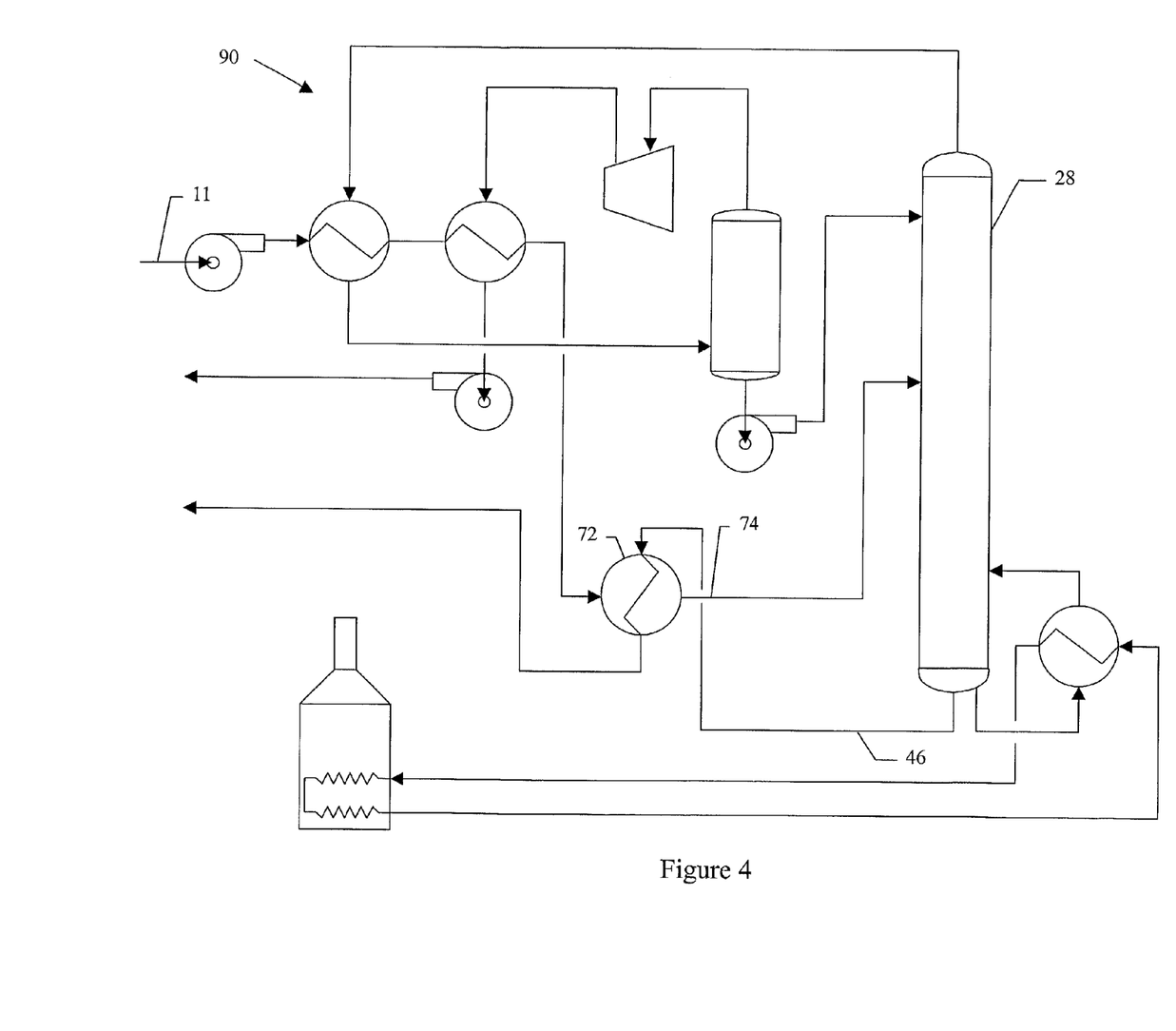
FIG. 4 is a flow diagram of an LNG processing unit arranged in accordance with a preferred embodiment of the present invention and including further heat integration without additional external heat input to the feed.

With reference to FIG. 4, LNG processing unit 90 takes advantage of elimination of the cooling utility as in LNG processing unit 70 and potentially reduces the capital cost of LNG processing unit 70 by eliminating feed preheater 62, shown in FIG. 3. LNG processing unit 90 may be appropriate where further feed preheat beyond what can be obtained with feed-bottoms heat exchanger 72 provides little or no benefit in reducing the diameter of tower 28. Thus, elimination of feed preheater 62 saves capital when the unit is constructed.

In LNG processing unit 90, third heated LNG feed stream 74 feeds tower 28 directly. No further preheat is necessary for third heated LNG feed stream 74. This operation will become more desirable as the molecular weight of bottoms stream 46 increases or as the quantity of bottoms stream 46 increases relative to LNG feed stream 11.

To illustrate the principles of the present invention, a set of data is included in Table I. The data set is presented merely by way of example and is not intended to limit the disclosure in any way. The data set is illustrates one exemplary embodiment of the present invention. The data set provides a mass and energy balance with reference to stream numbers indicated in LNG processing unit 70, shown in FIG. 3. NGL pump discharge stream 80 is the discharge of NGL pump 78 and is sent to an NGL pipeline for transport to distant locations. Overhead liquid stream 82 feeds reflux pump 26. The discharge of reflux pump 26 is reflux stream 84.

TABLE 1

| Stream # | Description | Pres. psia | Pres. kPa | Temp. °F. | Temp. °C. | MMSCF/ Day | MMm³/ Day | GPM | l/min |
|---|---|---|---|---|---|---|---|---|---|
| 11 | Pump Suct. | 150 | 1034 | −250 | −157 | 1200 | 34 | | |
| 14 | Pump Disc. | 400 | 2758 | −247 | −155 | 1200 | 34 | | |
| 18 | Ovhd. Vap. | 305 | 2103 | −144 | −98 | 1070 | 30 | | |
| 20 | 1st Heated Fd. | 395 | 2723 | −240 | −151 | 1200 | 34 | | |
| 22 | Cond. Ovhd | 300 | 2068 | −149 | −101 | 1070 | 30 | | |
| 30 | Ovhd. Prod. Vap. | 300 | 2068 | −148 | −100 | 1050 | 30 | | |
| 34 | Comp. Ovhd. Prod. | 500 | 3447 | −91 | −68 | 1050 | 30 | | |
| 38 | 2nd Heated Fd. | 390 | 2689 | −136 | −93 | 1200 | 34 | | |
| 40 | Cond. Ovhd. Prod. | 495 | 3413 | −134 | −92 | 1050 | 30 | | |
| 44 | Ovhd.from Pump | 1250 | 8618 | −114 | −81 | 1050 | 30 | | |
| 46 | Btms. | 317 | 2186 | 54 | 12 | | | 2800 | 10599 |
| 64 | Tower Fd. | 380 | 2620 | −130 | −90 | 1200 | 34 | | |
| 74 | 3rd Heated Fd. | 385 | 2654 | −134 | −92 | 1200 | 34 | | |
| 76 | Cool Btms. | 312 | 2151 | 0 | −18 | | | 2800 | 10599 |
| 80 | NGL Disc. | 1200 | 8274 | 15 | −9 | | | 2800 | 10599 |
| 82 | Ovhd.Liq. | 300 | 2068 | −149 | −101 | | | 250 | 946 |
| 84 | Rflx. from Pump | 350 | 2413 | −148 | −100 | | | 250 | 946 |

The above discussion is meant to be illustrative of the principles and various embodiments of present invention. Numerous variations and modifications will become apparent to those skilled in the art once the above disclosure is fully appreciated. For example, it will be obvious to one having ordinary skill in the art that feed-overhead heat exchanger 16 may be replaced by a refrigeration unit or other heat removal device with a corresponding loss in efficiency but without substantially changing the operation of the LNG processing unit as a whole. Similarly, use of hydraulic power recovery turbines and expanders could be used in the place of standard pressure drop inducing devices. Such modifications are within the scope of the present invention. Also, process control schemes for flow and distillation column control are well known to those having ordinary skill in the art and have not been shown in detail in this disclosure. Similarly, specific equipment sizing is well known to those having ordinary skill in the art. Thus, for example, details as to whether a given heat exchanger service requires a given number of shells (for a shell-and-tube heat exchanger) or a given number of plates (for a plate-and-frame heat exchanger) have not been spelled out both because sizing is well known in the art and because it is specific to a given application. It is intended that the following claims be interpreted to embrace all such variations and modifications.

What is claimed is:

1. A system for processing a liquefied natural gas feed comprising:
   a distillation column configured for multistage separation of said liquefied natural gas feed and configured to produce an overhead vapor stream and an ethane-rich product;
   a first heat exchanger configured to exchange heat between said overhead vapor stream of said distillation column and said liquefied natural gas feed, said first heat exchanger being configured to produce a first heated liquefied natural gas feed and a condensed overhead vapor stream;
   a separator configured to separate said condensed overhead vapor stream into an overhead vapor product and a liquid stream;
   a second heat exchanger configured to exchange heat between said first heated liquefied natural gas feed and said overhead vapor product.

2. The system of claim 1 wherein said second heat exchanger is configured to condense said overhead vapor product.

3. A system for processing a liquefied natural gas feed comprising:
   a distillation column configured for multistage separation of said liquefied natural gas feed and configured to produce an overhead vapor stream and an ethane-rich product;
   a first heat exchanger configured to exchange heat between said overhead vapor stream of said distillation column and said liquefied natural gas feed, said first heat exchanger being configured to produce a first heated liquefied natural gas feed and a condensed overhead vapor stream;
   a separator configured to separate said condensed overhead vapor stream into an overhead vapor product and a liquid stream;
   a second heat exchanger configured to exchange heat between said first heated liquefied natural gas feed and said overhead vapor product; and
   a compressor configured to compress said overhead vapor product before said overhead vapor product exchanges heat in said second heat exchanger.

4. The system of claim 3 further comprising a pump configured to pressurize said condensed overhead vapor product.

5. A system for processing a liquefied natural gas feed comprising:
   a distillation column configured for multistage separation of said liquefied natural gas feed and configured to produce an overhead vapor stream and an ethane-rich product;
   a first heat exchanger configured to exchange heat between said overhead vapor stream of said distillation column and said liquefied natural gas feed, said first heat exchanger being configured to produce a first heated liquefied natural gas feed and a condensed overhead vapor stream;
   a separator configured to separate said condensed overhead vapor stream into an overhead vapor product and a liquid stream;
   a second heat exchanger configured to exchange heat between said first heated liquefied natural gas feed and said overhead vapor product so as to produce a second heated liquefied natural gas feed; and
   a third heat exchanger, said third heat exchanger being configured to exchange heat between said ethane-rich product and said second heated liquefied natural gas feed.

6. The system of claim 5 wherein said third heat exchanger is configured to produce a third heated liquefied natural gas feed and wherein said system further comprises a fourth heat exchanger configured to heat said third heated liquefied natural gas feed to a desired energy level for feed to said distillation column.

7. The system of claim 6 further comprising a compressor configured to compress said overhead vapor product prior to said overhead vapor product entering said second heat exchanger and wherein said second heat exchanger is configured to condense said overhead vapor product.

8. A system for separating a liquefied natural gas stream into a methane-rich product and an ethane-rich product, said system comprising:
   a distillation column configured to fractionate said liquefied natural gas stream into an overhead vapor and said ethane-rich product;
   a compressor configured to compress said methane-rich product;
   a condenser configured to substantially condense said methane-rich product against said liquefied natural gas stream;
   a first heat exchanger configured to exchange heat from said overhead vapor with said liquefied natural gas stream before said liquefied natural gas stream is heated by any other heat exchanger; and
   a second heat exchanger configured to exchange heat from said ethane-rich product with said liquefied natural gas stream after said liquefied natural gas stream has been heated in said condenser.

9. A method for recovering ethane and heavier components from liquefied natural gas, the method comprising the steps of:
   (a) preheating said liquefied natural gas;
   (b) fractionating said liquefied natural gas into a overhead vapor stream and an ethane-rich product;
   (c) compressing a portion of the overhead vapor stream to form a compressed overhead vapor product stream; and
   (d) substantially condensing the compressed overhead vapor product stream;
   wherein step (a) comprises exchanging heat from said overhead vapor stream with said liquefied natural gas so as to form a condensed overhead vapor stream;
   wherein the condensed overhead vapor stream is separated into an overhead vapor product and a liquid stream;
   wherein step (c) comprises compressing the overhead vapor product; and
   wherein step (d) comprises exchanging heat from the compressed overhead vapor product with said liquefied natural gas.

10. The method of claim 9 wherein step (a) further comprises exchanging heat from said ethane-rich product with said liquefied natural gas.

11. The method of claim 10 wherein step (a) further comprises exchanging heat from said overhead vapor stream, the compressed overhead vapor product, and said ethane-rich product with said liquefied natural gas sequentially in order as listed.

12. A method for preheating liquefied natural gas for feed to a distillation column, wherein said distillation column produces an overhead vapor, and a bottoms product, the method comprising the steps of:
(a) exchanging heat from said overhead vapor with said liquefied natural gas so as to form a condensed overhead vapor stream;
(b) separating the condensed overhead vapor stream into an overhead vapor product and a liquid stream;
(c) compressing the overhead vapor product so as to form a compressed overhead vapor product; and
(d) exchanging heat from said compressed overhead vapor product with said liquefied natural gas.

13. The method of claim 12, further comprising:
(c) exchanging heat from said bottoms product with said liquefied natural gas.

14. The method of claim 12 wherein step (b) comprises condensing substantially all of said overhead vapor product.

15. The method of claim 14 wherein step (a) comprises condensing a portion of said overhead vapor.

16. The method of claim 12 wherein step (a) is performed before step (b).

17. The method of claim 14 further comprising:
(c) pumping said condensed overhead vapor product.

* * * * *